(12) United States Patent
Campagna et al.

(10) Patent No.: US 11,435,421 B2
(45) Date of Patent: Sep. 6, 2022

(54) ATTACHING PERIPHERAL COMPONENTS OF A MEDICAL IMAGING SYSTEM

(71) Applicant: Siemens Healthcare GmbH, Erlangen (DE)

(72) Inventors: Swen Campagna, Engelthal (DE); Philipp Höcht, Lauf (DE)

(73) Assignee: Siemens Healthcare GmbH, Erlangen (DE)

( * ) Notice: Subject to any disclaimer, the term of this patent is extended or adjusted under 35 U.S.C. 154(b) by 168 days.

(21) Appl. No.: 16/702,881

(22) Filed: Dec. 4, 2019

(65) Prior Publication Data
US 2020/0174091 A1 Jun. 4, 2020

(30) Foreign Application Priority Data
Dec. 4, 2018 (EP) .................................... 18209962

(51) Int. Cl.
| | | |
|---|---|---|
| *G06F 15/16* | (2006.01) | |
| *G01R 33/54* | (2006.01) | |
| *G06F 13/10* | (2006.01) | |
| *H04L 69/323* | (2022.01) | |
| *H04L 69/324* | (2022.01) | |
| *H04L 69/326* | (2022.01) | |
| *H04L 69/329* | (2022.01) | |

(52) U.S. Cl.
CPC ......... *G01R 33/543* (2013.01); *G06F 13/102* (2013.01); *H04L 69/323* (2013.01); *H04L 69/324* (2013.01); *H04L 69/326* (2013.01); *H04L 69/329* (2013.01)

(58) Field of Classification Search
CPC ... G01R 33/543; G06F 13/102; H04L 69/323; H04L 69/324; H04L 69/326; H04L 69/329
USPC ......................................................... 709/203
See application file for complete search history.

(56) References Cited

U.S. PATENT DOCUMENTS

| | | | | |
|---|---|---|---|---|
| 6,356,780 B1 * | 3/2002 | Licato | ................... | G16H 40/63 600/407 |
| 2001/0035866 A1 * | 11/2001 | Finger | ................. | G01S 7/52057 345/568 |
| 2002/0123672 A1 * | 9/2002 | Christophersom | .......................... | A61N 1/37282 600/300 |
| 2005/0138258 A1 | 6/2005 | Seto | | |
| 2015/0331830 A1 | 11/2015 | Kumar | | |
| 2017/0336635 A1 * | 11/2017 | Yoon | ................. | H04N 21/42203 |

FOREIGN PATENT DOCUMENTS

| | | |
|---|---|---|
| EP | 1700226 A1 | 9/2006 |
| WO | 2005064482 A1 | 7/2005 |

OTHER PUBLICATIONS

European Search Report for European Patent Application No. 18209962.2-1126 dated Jun. 19, 2019.

* cited by examiner

*Primary Examiner* — Duyen M Doan
(74) *Attorney, Agent, or Firm* — Lempia Summerfield Katz LLC

(57) ABSTRACT

One or more peripheral components are attached to a medical imaging system. One or more devices are attached to the one or more peripheral components and configured to communicate data with a controller of the medical imaging system.

20 Claims, 3 Drawing Sheets

(Reference Implementation)

ATTACHING PERIPHERAL COMPONENTS OF A MEDICAL IMAGING SYSTEM

This application claims the benefit of European Patent Application No. EP 18209962, filed on Dec. 4, 2018, which is hereby incorporated by reference in its entirety.

BACKGROUND

The present embodiments relate to a medical imaging system including one or more peripheral components and a device attached to such a peripheral component.

Medical imaging systems (e.g., magnetic resonance imaging (MRI) systems or computer tomography (CT) imaging systems) are widespread. Often, such medical imaging systems implement a modular approach in which various peripheral components may be selectively attached or detached to and from the medical imaging system. In this regard, the medical imaging system typically includes a central control unit that is configured to control operation of the medical imaging system based on data associated with the attached peripheral components.

Attaching peripheral components to the medical imaging system becomes more complex as the number of possible peripheral components increases. For example, different peripheral components may employ different communication protocols or may require certain drivers to be provisioned. To provide compatibility with various peripheral components, in reference implementations, respective component-specific control logic is provisioned in the control unit. Maintenance and interoperability of such specific control logic in the control unit of the medical system is complex and error prone. For example, it may be required to service and maintain a large number of control logic for the various peripheral components.

SUMMARY AND DESCRIPTION

The scope of the present invention is defined solely by the appended claims and is not affected to any degree by the statements within this summary.

The present embodiments may obviate one or more of the drawbacks or limitations in the related art. For example, advanced techniques of attaching peripheral components to a medical imaging system are provided. As another example, advanced techniques that overcome or mitigate at least some of the above-identified restrictions and drawbacks are provided.

A medical imaging system includes a peripheral component and a control unit. The control unit is configured to control operation of the medical imaging system based on data associated with the peripheral component. Also, the medical imaging system includes a device. The device is attached to the peripheral component. The device is configured to communicate the data with the control unit.

For example, the device may receive at least a part of the data and/or may transmit at least a part of the data. Bi-directional communication is possible.

A device for a medical imaging system is configured to communicate data with a control unit of the medical imaging system. The data is associated with a peripheral component of the medical imaging system.

A method includes communicating data with a control unit of the medical imaging system. The data is associated with a peripheral component of the medical imaging system.

A computer program, a computer program product, and/or a computer-readable storage medium (e.g., a non-transitory computer-readable storage medium) are provided. The computer program, the computer program product, and/or the computer-readable storage medium include program code that may be executed by at least one processor. Executing the program code causes the at least one processor to perform a method. The method includes communicating data with a control unit of the medical imaging system. The data is associated with a peripheral component of the medical imaging system.

BRIEF DESCRIPTION OF THE DRAWINGS

It is to be understood that the features mentioned above and those yet to be explained below may be used not only in the respective combinations indicated, but also in other combinations, or in isolation without departing from the scope of the invention.

DETAILED DESCRIPTION

Figure 1:
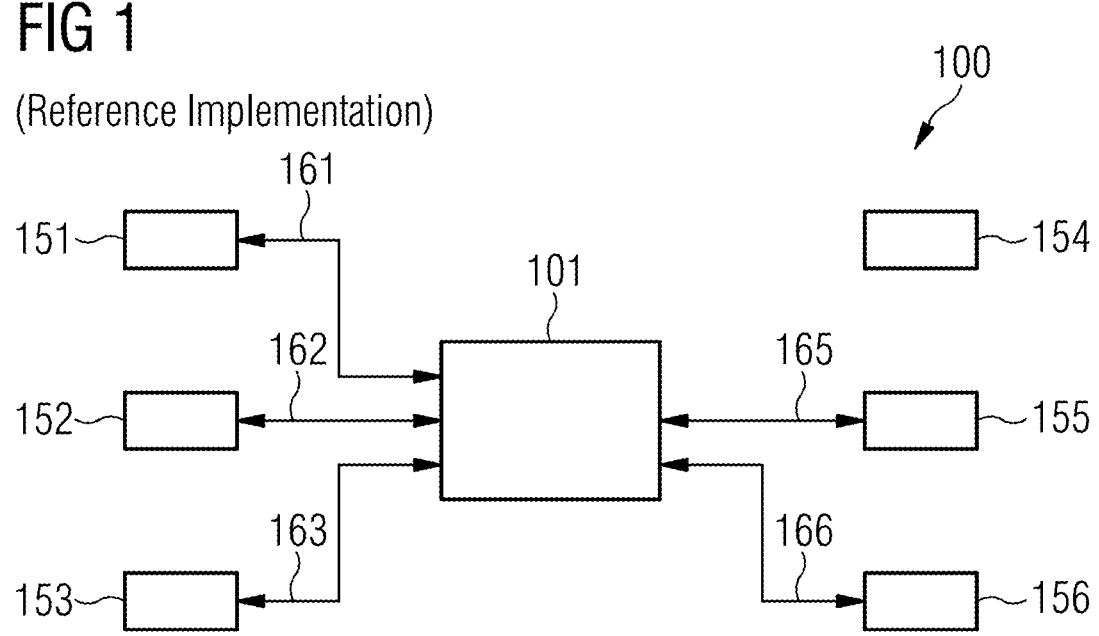
FIG. 1 is a schematic illustration of multiple exemplary peripheral components of a medical imaging system attached to a control unit of a medical imaging system.

In the following, embodiments will be described in detail with reference to the accompanying drawings. The following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that function and general purpose become apparent to a skilled person in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices are disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processing unit, integrated circuits, memory devices, read-only memory, electrically programmable read-only memory, electrically erasable programmable read-only memory, or other suitable variance thereof, and software that co-act with one another to perform operations disclosed herein. In addition, one or more of the electrical devices may be configured to execute a program code that is embodied in a non-transitory computer readable medium program to perform any number of the functions as disclosed.

Various examples described herein relate to attaching one or more peripheral components to a medical imaging system. Generally, a wide variety of medical imaging systems operating in a modular manner may be subject to the techniques described herein. For example, medical imaging systems may be any one of the following: magnetic resonance imaging (MRI) systems; x-ray imaging systems; CT imaging systems; positron emission tomography imaging systems; etc. For sake of simplicity, hereinafter, reference is made to an MRI system, while similar techniques may be readily applied to different types and kinds of medical imaging systems.

Attaching one or more peripheral components may include one or more of the following: establishing a mechanical connection between a body of the MRI system and the respective peripheral component(s); establishing an electrical connection between the respective peripheral component(s) and a control unit of the MRI system, hence acting as a core control unit; registering the peripheral component(s) at the core control unit of the MRI system.

As a general rule, the peripheral component may be a mechanical component and may optionally include electric circuitry. The electric circuitry may, in some scenarios, be used to control the operation of the peripheral component. In some scenarios, the peripheral component may not include electric circuitry, but rather be a mechanics-only part. An example would be a certain spacer for body placement in the MRI system or a phantom measurement device for calibration purposes. Such mechanical-only parts may be registered with the control unit of the MRI system (e.g., to adapt the operation of the MRI system accordingly). For example, a type or serial number of the peripheral component may be registered with the control unit of the MRI system.

To give a few non-limiting examples of peripheral components of an MRI system: resonance frequency (RF) coil; RF coil array; camera; loudspeaker; earphones; lighting equipment; gradient coils; cooling system; power amplifier; sensors; etc.

The control unit of the MRI system may implement control functionality for the operation of the medical imaging system. For this, the control unit may include one or more processors, non-volatile memories such as random access memory, and one or more communication interfaces. For example, the control unit may include a host computer, a low-level control system, and a control and recognition computer. The control unit is sometimes also referred to as core of the MRI system.

FIG. 1 schematically illustrates one embodiment of an MRI system 100 including a control unit 101 (e.g., a controller) and multiple peripheral components 151-156. FIG. 1 schematically illustrates aspects with respect to attaching the peripheral components 151-156 according to reference implementations.

Communication links 161-163, 165-166 are established between the control unit 101 and some of the peripheral components 151-153, 155-156. Example peripheral components include: a cooling system; a patient table; sensors for humidity, temperature, etc.; an uninterruptible power supply, monitoring unit; a radio frequency power amplifier; a magnet; and a camera.

In the example of FIG. 1, the peripheral components 151-153, 155-156 are connected using respective communication links 161-163, 165-166 with the control unit 101. These communication links 161-163, 165-166 generally depend on the respective peripheral component 151-153, 155-156. Each of the communication links 161-163, 165-166 may employ one or more specific protocols for communicating respective data. Example protocols include: controller area network (CAN); RS-232; universal serial bus (USB); I²C; and Ethernet.

As will be appreciated, such protocols may be generally defined on a transport-oriented layer according to the Open Systems Interface (OSI) model. See, for example, ITU-T X.200 (07/1994). The transport-oriented layers are also sometimes referred to as media layers. The transport-oriented layers are generally at the bottom of the respective layer stack. Examples of transport-oriented layers include physical layer, data link layer, network layer, and transport layer. Different, application-oriented layers are generally arranged at the top of the layer stack and, for example, include session layer, presentation layer, and application layer.

The protocols may, alternatively or additionally, also be defined on one or more application-oriented layers. For example, a certain HTML or XML code format may be defined for control commands on an application-oriented layer.

Drivers that control the operation of the respective peripheral component 151-153, 155-156 may be used. Such drivers are typically proprietary and depend strongly on the used operating system. A reason for this is that the respective data fed to the data link layer or the physical layer may vary from peripheral component to peripheral component. For example, certain commercial off-the-shelf peripheral components (e.g., RF power amplifiers) may implement proprietary application-oriented layers of the respective communication protocols, even if the lower layers implement a certain standardized protocol such as CAN or the like. For example, higher-layer data, data content and data formats, status messages, etc. may vary. All this may be captured by using the appropriate driver.

Besides such differences on an application-oriented layer, alternatively or additionally, the protocol may vary on lower layers (e.g., there may be different versions of CAN). This provides that it is not straightforward to exchange a first version of an RF power amplifier peripheral component 155 with a second version of an RF power amplifier peripheral component 155, because the software executed by the control unit 101 would have to be adapted.

A further example in this regard would be a camera peripheral component 156. Typically, the camera peripheral component 156 may be interfaced using a USB protocol on the transport-oriented layers, specifically the physical layer and the data link layer. Higher-layer functionality is then implemented by a driver associated with the respective camera peripheral component 156. The driver is typically tied to a certain operating system. Thus, if the operating system used by the computer of the control unit 101 supports the driver, then it is possible to transmit and/or receive (e.g., communicate) data to and from the camera peripheral component 156. Computers of the control unit 101 are sometimes exchanged over the lifetime of the MRI system 100. The camera peripheral component 156 is not changed at all times when the computer of the control unit 101 is exchanged. Then, when attaching the camera peripheral component 156 using the reference implementation of FIG. 1, a situation may be encountered in which the new computer of the control unit 101 uses another operating system for which a driver associated with the camera peripheral component 156 is not available. Since the driver implements very specific functionality such as asset data, status messages, loadware updates, etc. (or, generally, on an application-oriented layer), it is not simply possible to continue operation of the camera peripheral component 156 using the new operating system of the new computer of the control unit 101.

Another issue is that certain protocols (e.g., RS-232) are not supported by a wide range of computers. Sometimes, modern versions of the peripheral components then implement a different lower-layer protocol on the transport-layers. To provide interoperability and backwards compatibility, it may then sometimes limit the possibility to employ such modern versions of the peripheral components that do not employ the old RS-232 protocol.

FIG. 1 also illustrates a peripheral component 154 that does not have a communication interface. Data may not be communicated on a respective communication link between the peripheral component 154 and the control unit 101. Then, manual registration of the peripheral component 154 may be required to attach the peripheral component 154 to the MRI system 100.

As will be appreciated from the explanation of the reference implementation of attachment of peripheral components 151-156 given above, various interoperability issues may arise. To mitigate such interoperability issues, according to various examples, an interface (IF) device (e.g., a device) that supports the attachment of one or more respective peripheral components is employed. Aspects with respect to such an IF device are illustrated in connection with FIG. 2.

Figure 2:
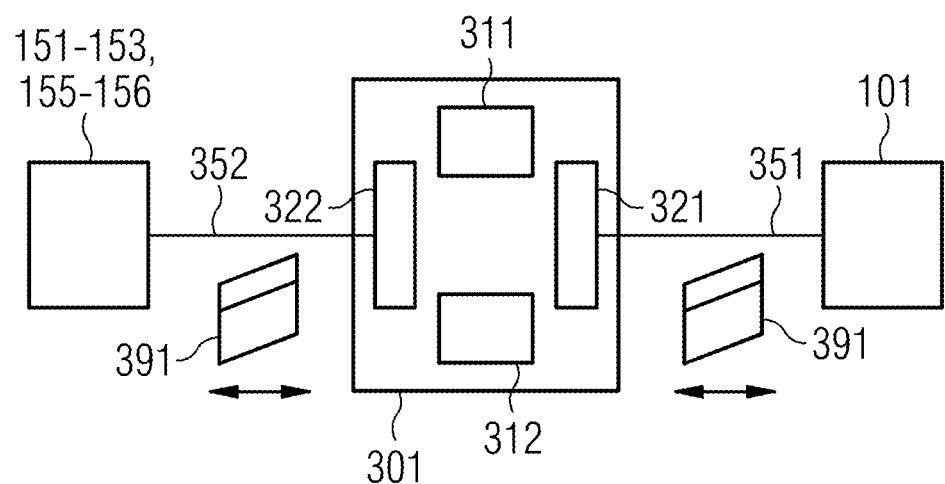
FIG. 2 schematically illustrates one embodiment of a device configured to communicate data associated with a peripheral component with the control unit of the medical imaging system.

FIG. 2 illustrates aspects with respect to an IF device 301. The IF device 301 includes a programmable logic 311 (e.g., a processor, an application specific integrated circuit (ASIC), or a field-programmable gate array (FPGA)), and a memory 312 such as a random-access memory and a non-volatile memory. Also, the IF device 301 includes a communication interface 321 for communicating with the control unit 101. The IF device 301 also includes an interface 322 for communicating with the respective peripheral component 151-153, 155-156. Generally, the interface 322 is optional.

As illustrated in FIG. 2, data 391 is communicated between the IF device 301 and the control unit 101. The data 391 may be used by the control unit 101 to control operation of the MRI system 101.

Optionally, the data 391 may also be communicated between the control unit 301 and the respective peripheral component 151-153, 155-156. For example, the data 391 may be forwarded between the respective peripheral component 151-153, 155-156 and the control unit 101. This applies, specifically, to "smart" peripheral components 151-153, 155-156 that have communication circuitry available.

In other examples, at least a part of the data 391 may be generated/consumed by the IF device 301 (e.g., at least a part of the data 391 received from the control unit 101 may be stored to the memory 312 (but not forwarded), and/or at least a part of the data 391 transmitted to the control unit 101 is loaded from the memory 312). An associated communication link terminates at the IF device 301. Such a scenario may be, for example, applicable in connection with a peripheral component that does not, per se, include electrical circuitry or a communication interface (cf., peripheral component 154 in the scenario of FIG. 1). In such a scenario, the IF device 301 complements functionality of the peripheral component 154. For example, a serial number or type number of the peripheral component 154 may be loaded from the memory 312 and communicated as data 391 to the control unit 101. This facilitates automated registration of the respective peripheral component 154.

As illustrated in FIG. 2, generally, bi-directional communication of the data 391 is possible (e.g., to or from the control unit 101). Hence, the data 391 may include an uplink part transmitted by the IF device 301 and received by the control unit 101, and/or may include a downlink part transmitted by the control unit 101 and received by the IF device 301.

Next, the integration of such an IF device 301 into the MRI system 100 is illustrated in detail in connection with FIG. 3.

Figure 3:
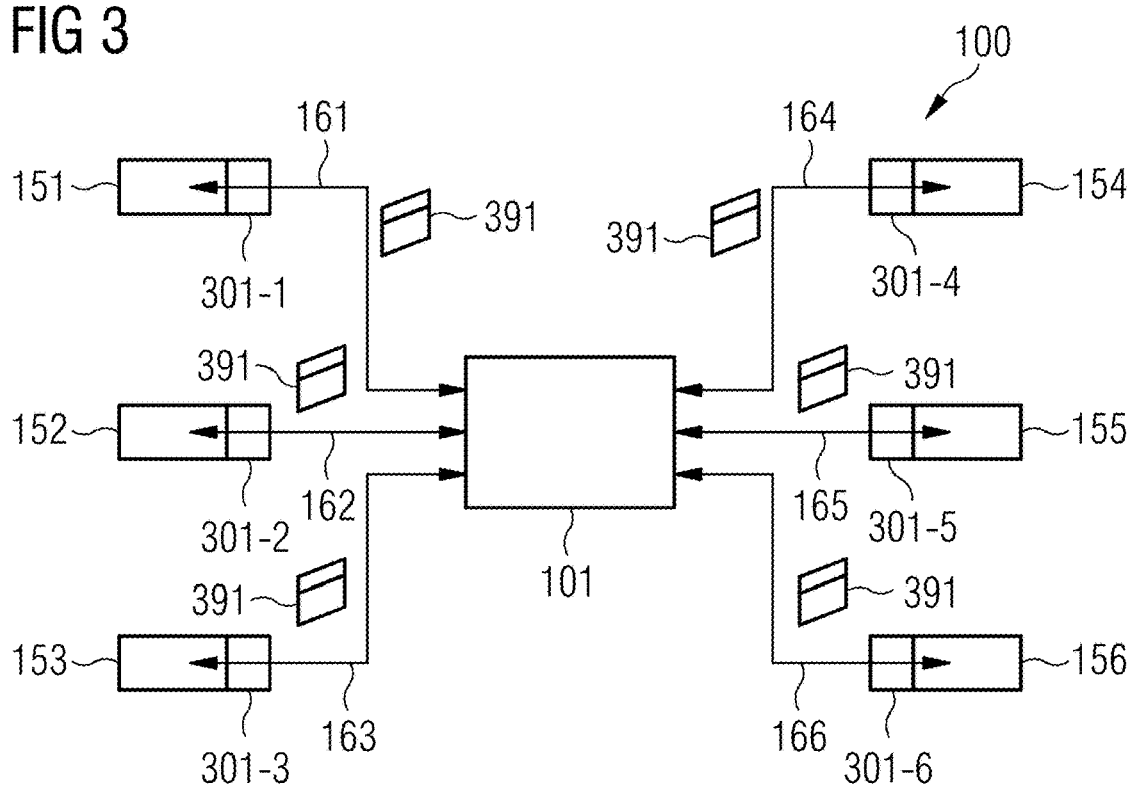
FIG. 3 schematically illustrates an exemplary attachment of multiple peripheral components to a control unit of a medical imaging system using devices according to FIG. 2.

FIG. 3 schematically illustrates aspects with respect to the MRI system 100. FIG. 3 generally corresponds to FIG. 1. However, in the example of FIG. 3, the attachment of the peripheral components 151-156 is in accordance with various examples.

In FIG. 3, each peripheral component 151-156 has a respective IF device 301-1-301-6 attached thereto. Each of the IF devices 301-1-301-6 may be configured as explained in connection with the IF device 301 of FIG. 2. Specifically, each IF device 301-1-301-6 may be configured to communicate the data 391 with the control unit 101.

The attachment of the IF devices 301-1-301-6 to the peripheral components 151-156 may be mechanically implemented. For example, the respective IF device 301-1-301-6 may be mounted to a housing of the corresponding peripheral component 151-156 or may be integrated into the housing of the respective peripheral component 151-156. For example, commercial off-the-shelf peripheral components may thereby be complemented by the respective IF device 301-1-301-6.

The attachment of at least some of the IF devices 301-1-301-6 to the peripheral components 151-153, 155-156 may be electrical. For example, for peripheral components 151-153, 155-156, respective communication links 161-163, 165-166 between the control unit 101 and the corresponding peripheral component 151-153, 155-156 are via the respective IF device 301-1-301-3, 301-5-301-6. Differently, the control link 164 for the data 391 associated with the peripheral component 154 terminates at the associated IF device 301-4, because the peripheral component 154 does not have a communication interface. There is no electrical attachment of the peripheral component 154 to the respective IF device 301-4, but merely a mechanical attachment.

The control unit 101 may control the operation of the MRI system 100 using the data 391 associated with the various peripheral components 151-156. Specifically, for the peripheral components 151-153, 155-156, it would be possible that the control unit 101 also controls operation of the respective peripheral components 151-153, 155-156 using the respective data 391. For example, an operating mode of the peripheral components 151-153, 155-156 may be switched, data acquisition or signal playout may be triggered, a sleep mode may be activated; etc., to give just a few examples. The kind of operational control may vary with the type of peripheral component 151-153, 155-156.

Thus, as a general rule, the data 391 may relate to control commands for the operation of the MRI system 100 or the respective peripheral component 151-153, 155-156, status messages, download or uplink functionality, or standardized hardware interfaces.

Using the IF devices 301-1-301-6, operation of the peripheral component 151-156 may be separated, to some degree, from operation of the central control unit 101. Specifically, a unified approach may be implemented for communication of the data 391 associated with the various peripheral components 301-1-301-6. Component-specific logic may be provisioned at the IF devices 301-1-301-6, rather than at the control unit 101.

The advantage is that additional control logic that is specific to each individual peripheral component 151-156 may not be required to be provisioned at the control unit 101. The control unit 101 may thereby be implemented in a simple and less complex manner (e.g., if compared to reference implementations of component attachment according to FIG. 1). Frequent changes or updates to the control unit 101, specifically to the software, are avoided. This facilitates maintenance of the control unit 101 and reduces downtime or fault states of the MRI system 100. Respective control logic is moved from the control unit 101 to the IF devices 301-1-301-6.

For example, a well-defined protocol towards the control unit 101 may be provided on the respective communication link 161-166. For example, the same protocol(s) may be provided on all of the communication links 161-166. Thereby, a need for individually adapting the software of the control unit 101 for each individual protocol supported by the peripheral components 151-153, 155-156 is mitigated. A corresponding adaption/conversion may then be implemented by the IF devices 301-1-301-6. The control unit 101 still communicates with the peripheral components 151-153, 155-156, but through the IF devices 301-1-301-6. Operation of the IF devices 301-1-301-3, 301-5-301-6 may be transparent to the operation of the control unit 101 (e.g., transparent to a function executed by the control unit 101 to control the operation of the MRI system 100 based on the respective data 391). The IF device may act as a transponder to facilitate the respective communication link 161-163, 165-166. The IF device may even complement respective controlling functionality for controlling 164 associated with the peripheral component 154, which, per se, does not support communication of the respective data 391. By using such a standardized protocol for implementing the communication links 161-166, development validation and revalidation and backend tests for new or changed peripheral components 151-156 are significantly simplified.

By using a small and compact computer for the IF devices 301-1-301-6, corresponding hardware may be re-used. Software executed by the respective IF device 301-1-301-6 may be adapted to the respective associated peripheral component 151-156. For example, an operating system executed by the IF device 301-1-301-6 may be chosen to support execution of a driver associated with the respective peripheral component 151-156. Thus, the same hardware of the IF device 301-1-301-6 may be reused for various peripheral components 151-156. The IF device 301 may be provided with a communication protocol 322 that supports various protocols 352 towards the peripheral components. Example protocol 352 may include CAN, RS-232, General Purpose Input Output (GPIO), Ethernet, USB, etc. Different operating systems may be executed by the processor 311 (e.g., Windows or Linux).

Different peripheral components 151-153, 155-156 may use different protocols 352. At the same time, only a smaller number or even a single protocol 351 may be used towards the control unit 101.

From the perspective of the control unit 101, there may be a single loadware executing a function to exchange the data 391 for each peripheral component 151-156. The operation of the respective IF device 301-1-301-6 may be transparent to the operation of the respective IF device 301-1-301-6. Encapsulation of the operation of the IF device 301-1-301-6 from the perspective of the corresponding function executed by the control unit 101 is possible. For example, the function executed by the control unit 101 may be irrespective of the particular operating system executed by the processor 311 of the corresponding IF device 301-1-301-6. Thereby, a legacy Windows USB driver may be executed by the control unit 101 for a longer time duration even if, for example, the operating system is changed on the control unit 101 and/or the control unit 101 is not compatible with the respective operating system executed by the IF device 301-1-301-6. Thus, as a general rule, while the processor 311 of the IF device 301-1-301-6 may use a first operating system, the control unit 101 may use a second operating system that is different from the first operating system. Software development thereby is transferred to the IF device 301-1-301-6, away from the control unit 101. Modular hardware and mainline software may be employed. The respective IF device 301-1-301-6 may be adapted by its software to the individual requirements of each respective peripheral component 151-156. This applies to, for example, proprietary loadware updates, adaptation of representation of the data 391 or asset data, etc. Even in the case of peripheral components 154 that do not include a respective communication interface, the use of such an IF device 301-4 may be helpful. Asset data such as serial number, type number, etc. may be provided by the IF device 301-4 (e.g., loaded from its non-volatile memory 312). Thereby, auto configuration of the MRI system 100 becomes possible, and manual registration of the respective peripheral component 154 may not be required. In maintenance situations, the registration of peripheral components may be easily traced and tracked.

Figure 4:
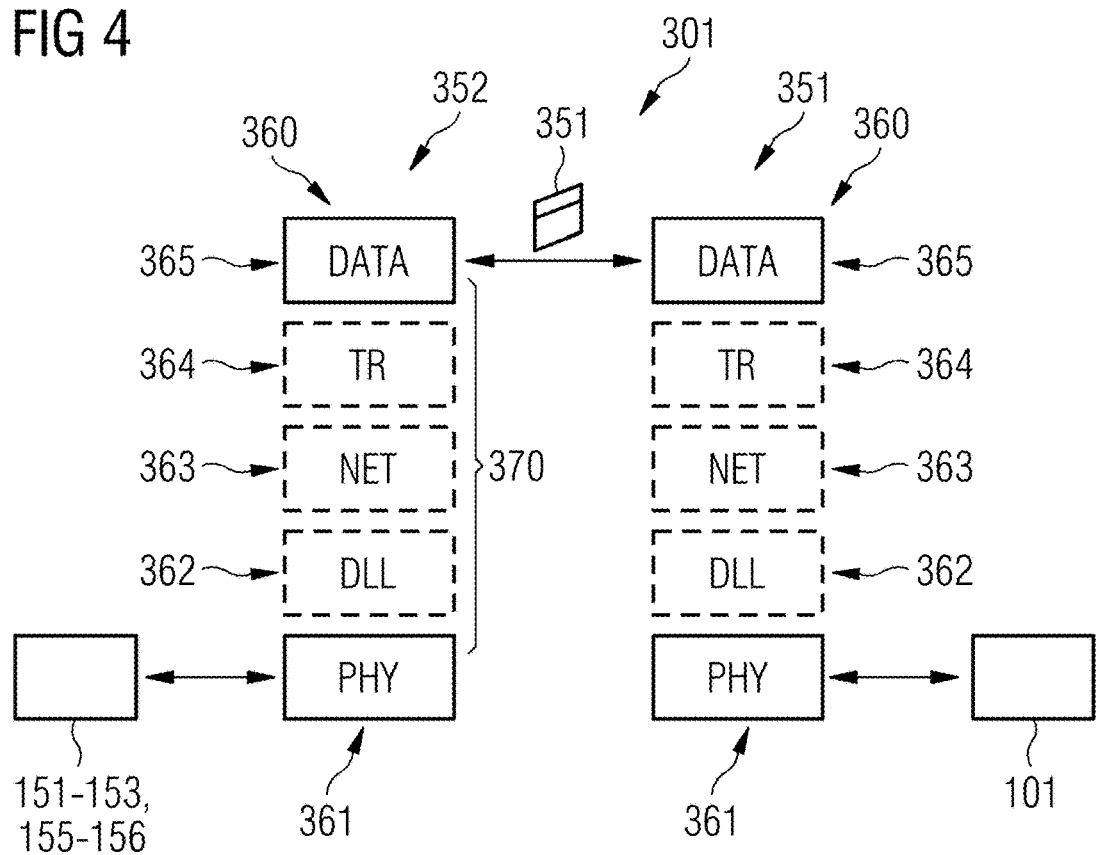
FIG. 4 schematically illustrates an exemplary conversion functionality of the device according to FIG. 2.

FIG. 4 schematically illustrates aspects with respect to the function of the IF device 301. While FIG. 4 illustrates techniques for the IF device 301, similar techniques may be readily employed for any one of the IF devices 301-1-301-3, 301-5-301-6.

In FIG. 4, a conversion functionality of the IF device 301 between the protocol 351 used for communication with the control unit 101 and the protocol 352 used for communication with the respective peripheral component 151-153, 155-156 is illustrated. In the example of FIG. 4, the IF device 301 is configured to convert the data 351 on transport-oriented layers 361-364 and on an application-oriented layer 365 of the protocols 351, 352. The protocols 351, 352 define the respective communication link 161-163, 165-166. For example, the control unit 101 may transmit the data 351, and the data 351 may be forwarded by the IF device 301 to the respective peripheral component 151-153, 155-156.

In the example scenario of FIG. 4, a representation of the data 351 on the physical layer 361 is received, and then traverses the various transport-oriented layers (e.g., the physical layer 361, the data link layer 362, the network layer 363, and the transport layer 364). For example, the layers 361 and 362 may be in accordance with the Ethernet standard according to IEEE 802.3. For example, the network layer 363 of the protocol 351 may be in accordance with the Internet Protocol (e.g., Internet Protocol version 4 of RFC 791). For example, the transport layer 364 of the protocol 351 may be in accordance with the transmission control protocol (TCP).

Then, on application layer 365, an XML document, for example, may define the data 351. The conversion may then occur by using a driver 370 that transforms the data 351 on the application layer to a respective representation on the physical layer 361 of the protocol 352. For example, the physical layer 361 and the data link layer 362 of the protocol 352 may be in accordance with the USB protocol. In such a scenario, the protocol 352 does not need to include the further transport-oriented layers 363 and 364.

As a general rule, the protocol 352 may only include the physical layer 361, but does not include the data link layer 362, the network layer 363, and the transport layer 364. For example, such a situation may be encountered where a simple voltage signal that controls a, for example, sensor peripheral component is output.

The driver 370 has the task of initializing and configuring operation of the respective peripheral component 151-153, 155-156, for example, by sending, via the physical layer 361, respective initialization or reset commands.

The driver 370 also obtains or outputs a representation of the data 351 on the application-oriented layer 365 of the protocol 351 and outputs or receives a representation of the data 351 on, for example, the physical layer 361 or the data link layer 362 of the protocol 352.

To give a specific example, a camera peripheral component 151 outputs image data via USB. USB defines the physical layer 361 and the data link layer 362 of the protocol 352. The protocol 352 may not implement the network layer and the transport layer 363, 364. The driver 370 may initialize the camera and trigger an acquisition command and then, based on an output of the data link layer 362, may provide the image as data 352 on the application-oriented layer 365. The image may be stored in a first format (e.g., PNG or TIFF). Then, a conversion may be implemented by the driver 370 or another function of the IF device 301 to provide the image in another format for the protocol 351 on the respective application-oriented layer 365 (e.g., JPG). Then, the data 351 (e.g., the converted image data) may be transmitted to the control unit 101 by traversing the layers 364 to 361 of the protocol 351.

While this specific example has been illustrated for an uplink part of the data 351, respective scenarios for downlink parts of the data 351 may also be provided. For example, in connection with the example of an imaging peripheral component, a command to execute movie acquisition at a given frame rate may be issued by the control unit 101 and encoded in an XML document as the data 351. Then, a conversion may be implemented by the driver 370 or another function of the IF device 301 to provide the corresponding control command in a format that is readable by the camera peripheral component. The driver 370 may then translate that format of the data 351 to an input on the data link layer 362 according to the USB protocol.

Further, while in connection with FIG. 4, a scenario has been explained in which conversion is both on the transport-oriented layers 361-364 as well as on the application-oriented layer 365 of the protocols 351, 352, in other examples, the conversion may only be on one of the transport-oriented layer(s) 361-364 and the application-oriented layer(s) 365. For example, a scenario may occur where the application-layer representation of the data 351 transmitted by the control unit 101 is directly understandable by the respective peripheral component 151-153, 155-156, or vice versa; here, a conversion of, for example, an image file or an xml file, etc. on the application-oriented layer(s) 365 is not required. The conversion may be solely on the application-oriented layer(s) 365, but not on the transport-oriented layer(s) 361-364. For example, this may apply to a scenario where the protocols 351, 352 both use Ethernet or USB, etc. but the application-layer representation of the data 351 is to be converted.

Figure 5:
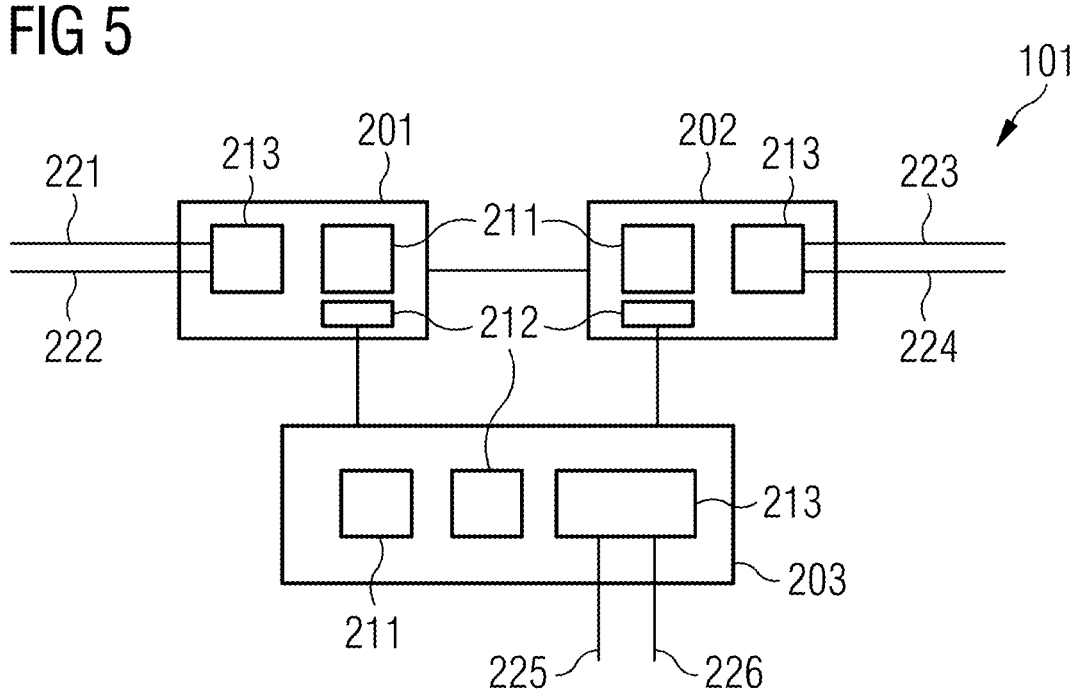
FIG. 5 schematically illustrates one embodiment of the control unit of the medical imaging system.

FIG. 5 illustrates aspects in connection with the control unit 101. As illustrated in the scenario of FIG. 5, the control unit 101 includes a host computer 201, a control and recognition computer 202, and an MR control computer 203. Each of the computers 201-203 includes a respective processor 211 and a memory 212 that may store associated program code executable by the respective processor 201. Each one of the computers 201-203, in the example of FIG. 5, also includes a communication interface 213. These communication interfaces 213 respectively support corresponding protocols 221-226. In some scenarios, each of the communication interfaces 213 may support the same one or more communication protocols 221-226 (e.g., Ethernet and USB or the like). The different communication interfaces 213 may support different communication protocols 221-226. These communication protocols 221-226 may match with or correspond to the protocol 351, as discussed in connection with FIG. 4 above.

Figure 6:
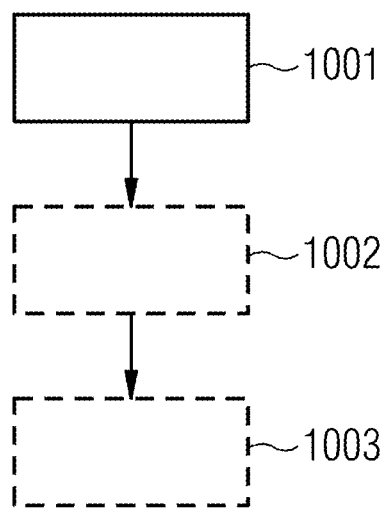
FIG. 6 is a flowchart of one embodiment of a method.

FIG. 6 is a flowchart of a method according to various examples. For example, the flowchart of FIG. 6 may be executed by an IF device for a medical imaging system (e.g., an MRI 100 according to the various examples described herein). For example, the method of FIG. 6 may be executed by one of the IF devices 301, 301-1-301-6, as discussed in connection with the preceding figures. For example, a processor of such an IF device (cf., FIG. 2, processor 311) may load program code from a memory (cf., FIG. 2, memory 312) and then execute, based on the program code, the method according to FIG. 6. For example, the program code may also be loaded from a computer program product or a computer-readable medium.

In block 1001, the IF device transmits and/or receives (e.g., communicates) data with a control unit of the medical imaging system. For example, uplink and/or downlink data may be communicated. For example, the communication may be in accordance with a first protocol. The protocol may include one or more transport-oriented layers of a corresponding layer stack. The protocol may include one or more application-oriented layers of the layer stack.

In some examples, the data that is communicated in block 1001 may be stored in or received from a memory of the IF device. In such scenarios, the IF device may act as a data originator or data sink. Such a scenario may be helpful where a peripheral component associated with the data, per se, does not include communication functionality. However, in other examples, the data communicated in block 1001 may be converted from the first protocol to a second protocol (e.g., on a transport-oriented layer of the second protocol and/or on an application-oriented layer of the second protocol) in block 1002.

This conversion may be, for example, performed by a driver that is executed by the IF device, block 1003. For example, a corresponding operating system may be used to execute the driver in block 1003. The converted data of block 1002 may then be forwarded to the control unit or the peripheral component, depending on the directivity of the communication.

Although the invention has been shown and described with respect to certain exemplary embodiments, equivalents and modifications will occur to others skilled in the art upon the reading and understanding of the specification. The present invention includes all such equivalents and modifications and is limited only by the scope of the appended claims.

For example, while various techniques have been described in connection with an MRI system, similar techniques may be readily applied to other kinds and types of medical imaging systems. While various scenarios have been described in connection with specific peripheral components, other types and kinds of peripheral components may be used.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging system comprising:
a peripheral component;
a controller configured to control operation of the medical imaging system based on data associated with the peripheral component; and
a device attached to the peripheral component and configured to communicate the data with the controller, wherein the device comprises a hardware processor, the hardware processor being configured to execute a driver associated with the peripheral component, and
wherein the device is configured to convert data on an application-oriented layer of one or more protocols of a communication link between the peripheral component and the controller via the device, the conversion of the data on the application-oriented layer including an application-oriented conversion including data content and status messages.

2. The medical imaging system of claim 1, further comprising:
the communication link between the peripheral component and the controller via the device,
wherein the controller is configured to control operation of the peripheral component based on the data communicated on the communication link.

3. The medical imaging system of claim 2, wherein the device is further configured to convert the data on a transport-oriented layer of the one or more protocols of the communication link.

4. The medical imaging system of claim 2, wherein the communication link comprises a first protocol for a first communication, the first communication being with the controller, and
wherein the communication link further comprises a second protocol for a second communication, the second communication being between an adapter and the peripheral component.

5. The medical imaging system of claim 4, wherein the second protocol comprises a physical layer.

6. The medical imaging system of claim 5, wherein the second protocol comprises a data link layer.

7. The medical imaging system of claim 6, wherein the driver is configured to obtain or output a representation of the data on an application-oriented layer of the first protocol and output or receive a representation of the data on the physical layer or the data link layer of the second protocol.

8. The medical imaging system of claim 4, wherein the peripheral device is a first peripheral device, the device is a first device, and the communication link is a first communication link,
wherein the medical imaging system further comprises:
a second peripheral component;
a second device attached to the second peripheral component and configured to communicate further data with the controller; and
a second communication link between the second peripheral component and the controller via the second device,
wherein the controller is configured to control operation of the second peripheral component based on the further data communicated on the second communication link,
wherein the second communication link comprises a third protocol for a third communication, the third communication being between the controller and the second device, and further comprises a fourth protocol for a fourth communication, the fourth communication being between the second device and the second peripheral component, and
wherein the second protocol is different than the fourth protocol.

9. The medical imaging system of claim 8, wherein the first protocol corresponds to the third protocol.

10. The medical imaging system of claim 1, wherein the device comprises a processor, the processor being configured to execute a driver associated with the peripheral component.

11. The medical imaging system of claim 10, wherein the processor is a first processor, the first processor being further configured to execute the driver using a first operating system, and
wherein the controller comprises a second processor, the second processor being configured to use a second operating system, the second operating system being different than the first operating system.

12. The medical imaging system of claim 1, wherein the controller is configured to execute a function to control operation of the medical imaging system based on the data, and
wherein operation of the device is transparent to the function.

13. The medical imaging system of claim 1, wherein the device comprises a programmable logic, a random-access memory, and at least one communication interface, the at least one communication interface being configured for communicating the data with the controller.

14. The medical imaging system of claim 13, wherein the at least one communication interface is configured for communicating the data with the peripheral component.

15. The medical imaging system of claim 1, wherein the device is configured to transmit an uplink part of the data to the controller, the device is configured to receive a downlink part of the data from the controller, or the device is configured to transmit the uplink part of the data to the controller and receive the downlink part of the data from the controller.

16. The medical imaging system of claim 15, wherein the device is configured to load or store at least a part of the data from a non-volatile memory of the device.

17. A device for a medical imaging system, the device comprising:
a hardware processor configured to: communicate data associated with a peripheral component of the medical imaging system with a controller of the medical imaging system;
execute a driver associated with the peripheral component; and
convert data on an application-oriented layer of one or more protocols of a communication link between the peripheral component and the controller, the conversion of the data on the application-oriented layer including an application-oriented conversion including data content and status messages.

18. The device of claim 17, wherein the device is attached to the peripheral component.

19. The device of claim 17, wherein the driver is configured to obtain or output a representation of the data on an application-oriented layer of a first protocol of the communication link between the peripheral component and the controller, and output or receive a representation of the data on a physical layer or a data link layer of a second protocol of the communication link.

20. A method comprising:
communicating, by a device attached to a peripheral component of a medical imaging system, data associated with the peripheral component with a controller of the medical imaging system;
executing, by a hardware processor of the device, a driver associated with the peripheral component; and
converting, by the device, data on an application-oriented layer of one or more protocols of a communication link between the peripheral component and the controller, the converting of the data on the application-oriented layer including application-oriented converting of data content and status messages.

\* \* \* \* \*